US012685556B2

(12) United States Patent
Fulchiero et al.

(10) Patent No.: US 12,685,556 B2
(45) Date of Patent: Jul. 21, 2026

(54) DEVICE AND METHOD FOR REMOVAL OF MOLLUSCUM CONTAGIOSUM

(71) Applicants: Judah Fulchiero, Altoona, PA (US); Gregory Fulchiero, Altoona, PA (US)

(72) Inventors: Judah Fulchiero, Altoona, PA (US); Gregory Fulchiero, Altoona, PA (US)

( * ) Notice: Subject to any disclaimer, the term of this patent is extended or adjusted under 35 U.S.C. 154(b) by 172 days.

(21) Appl. No.: 18/809,522

(22) Filed: Aug. 20, 2024

(65) Prior Publication Data
US 2026/0053527 A1 Feb. 26, 2026

(51) Int. Cl.
*A61B 17/3205* (2006.01)
*A61B 17/00* (2006.01)

(52) U.S. Cl.
CPC *A61B 17/3205* (2013.01); *A61B 2017/00761* (2013.01)

(58) Field of Classification Search
CPC ..... A61B 17/00; A61B 17/3205; A61B 17/54; A61B 17/322; A61B 2017/00761; A61B 2017/320004
See application file for complete search history.

(56) References Cited

U.S. PATENT DOCUMENTS

| | | | |
|---|---|---|---|
| 5,447,511 A | 9/1995 | Gadd | |
| 5,843,094 A | 12/1998 | Saylor | |
| 7,803,170 B2 * | 9/2010 | Mitusina | A61B 17/32002 606/171 |
| 8,679,097 B2 * | 3/2014 | Jorgensen | A61B 17/320016 606/1 |
| 11,471,364 B2 | 10/2022 | Rodan et al. | |
| 12,290,651 B2 | 5/2025 | Davidson et al. | |
| 2008/0038970 A1 | 2/2008 | Golta et al. | |
| 2014/0277043 A1 * | 9/2014 | Jenkins | A61B 17/24 134/6 |
| 2021/0275225 A1 | 9/2021 | Boone, III | |

FOREIGN PATENT DOCUMENTS

| | | |
|---|---|---|
| AU | 2003287921 B2 | 7/2004 |
| CN | 201481496 U | 5/2010 |
| CN | 202458571 U | 10/2012 |

(Continued)

OTHER PUBLICATIONS

"Sklar Molluscum Curette", medicaldevicedepot.com, Nov. 5, 2019, https://medicaldevicedepot.com/Sklar-Molluscum-Curette-p/06-4039.htm?dfw_tracker=3918-7585&gclid=CjwKCAjwxt_tBRAXEiwAENY8hfU8gR%E2%80%A6. Accessed Nov. 5, 2019.

*Primary Examiner* — Vi X Nguyen
(74) *Attorney, Agent, or Firm* — The Webb Law Firm

(57) ABSTRACT

Provided herein is a device for removing lesions, the device having an elongated body extending in two opposite directions, the elongated body terminating at a first end and a second end, a first cutting end at the first end of the elongated body, the first cutting end having a first cutting edge and a substantially flat lower surface, and a second cutting end at the second end of the elongated body having a first edge and a second edge, wherein the first cutting end comprises a slope, wherein the slope defines a downward and outward concave towards the flat lower surface of the first cutting end to form the first cutting edge, wherein the second cutting end comprises a slope, wherein the slope defines a first side surface and a second side surface between the lower face and upper surface of the second end.

9 Claims, 7 Drawing Sheets

(56)    References Cited

FOREIGN PATENT DOCUMENTS

| | | | |
|---|---|---|---|
| CN | 202589605 | U | 12/2012 |
| CN | 203609475 | U | 5/2014 |
| CN | 203776991 | U | 8/2014 |
| CN | 211357413 | U | 8/2020 |
| CN | 211410700 | U | 9/2020 |
| CN | 113082311 | A | 7/2021 |
| CN | 214285815 | U | 9/2021 |
| DE | 202010014741 | U1 | 2/2011 |
| EP | 1682015 | B1 | 1/2008 |
| EP | 2617375 | A1 | 7/2013 |
| WO | 2018232277 | A1 | 12/2018 |
| WO | 2020150459 | A1 | 7/2020 |
| WO | 2021128963 | A1 | 7/2021 |

* cited by examiner

DEVICE AND METHOD FOR REMOVAL OF MOLLUSCUM CONTAGIOSUM

BACKGROUND OF THE INVENTION

Field of the Invention

The present disclosure relates to a device and method for removal of molluscum contagiosum and other skin lesions and, more particularly, to a device with two improved cutting edges that provide axial gliding of the blades for removing molluscum contagiosum.

Description of Related Art

There are numerous instruments for treating the skin of a person. Depending on the specific type of the skin condition to be treated, the instruments differ. For example, specific instruments exist to treat skin conditions, such as acne, blisters, eczema, etc. For example, International Application Pub. No. WO2021/128963A1 is directed to a device for treating blackheads on skins. Additionally, other instruments exist to treat physical obtrusions to a skin, such as a splinter or ticks. U.S. Pat. Nos. 5,447,511 and 5,843,094 are directed to removing ticks anchored in the skin of a person or animals. Similarly, specific tools are needed to safely and effectively remove molluscum contagiosum.

SUMMARY OF THE INVENTION

Accordingly, provided are improved devices and methods for removing molluscum contagiosum.

In some non-limiting embodiments or aspects, provided is a device for removing lesions may include an elongated body extending in a first direction and a second direction opposite to the first direction, the elongated body terminating at a first end and a second end, a first cutting end at the first end of the elongated body, the first cutting end having a first cutting edge, an upper surface, and a substantially flat lower surface, and a second cutting end at the second end of the elongated body having an upper surface, a lower surface, and a second cutting edge.

In some non-limiting embodiments or aspects, the first cutting end may include a slope. The slope may extend in the first direction from the upper surface to the substantially flat lower surface of the first cutting end. The slope may terminate at the substantially flat lower surface to form the first cutting edge. The second cutting end may include a first side surface and a second side surface that extend in the second direction from the lower surface to the upper surface of the second cutting end. The first side surface and the second side surface may be formed between the lower face and upper surface of the second end. The first side surface and the second side surface may be substantially parallel to each other. The first side surface may terminate at the lower surface of the second end to form the second cutting edge.

In some non-limiting embodiments or aspects, the first cutting end and the second cutting end may be removably attached to the elongated body. The device may include a grip portion, wherein the elongated body includes the grip portion, and wherein the thickness of the grip portion of the elongated body may be constant. The first side surface and the second side surface may form an enclosed opening. The enclosed opening may be configured to receive a lesion, and wherein the first side surface and the second side surface may be interconnected.

In some non-limiting embodiments or aspects, the second end may include a contact portion. The contact portion may be configured to lift the elongated body such that the elongated body does not contact skin of a person when the first cutting end or the second cutting end is on contact with the skin of the person. The second end may extend in the second direction from the elongated body at an angle.

In some non-limiting embodiments or aspects, provided is a method of removing lesions. The method may include placing the first cutting edge of the device on skin of a person in vicinity of a lesion, lifting the grip portion of the device such that only the contact portion of the first end and the first end of the device are in contact with the person, and moving the first cutting edge laterally and in parallel with the skin of the person towards the lesion.

In some non-limiting embodiments or aspects a method of removing lesions may include placing the second cutting edge of the device on skin of a person in vicinity of a lesion, wherein the lesion is placed inside the opening, lifting the grip of the device such that only the contact portion of the second end and the second end of the device are in contact with the person, and moving the second cutting edge laterally and in parallel with the skin of the person towards the lesion.

DESCRIPTION OF THE DRAWINGS

Corresponding reference characters indicate corresponding parts throughout the several views. The embodiments set out herein illustrate exemplary aspects of the disclosure, and such embodiments are not to be construed as limiting the scope of the disclosure in any manner.

DESCRIPTION OF PREFERRED EMBODIMENTS

Figure 1A:
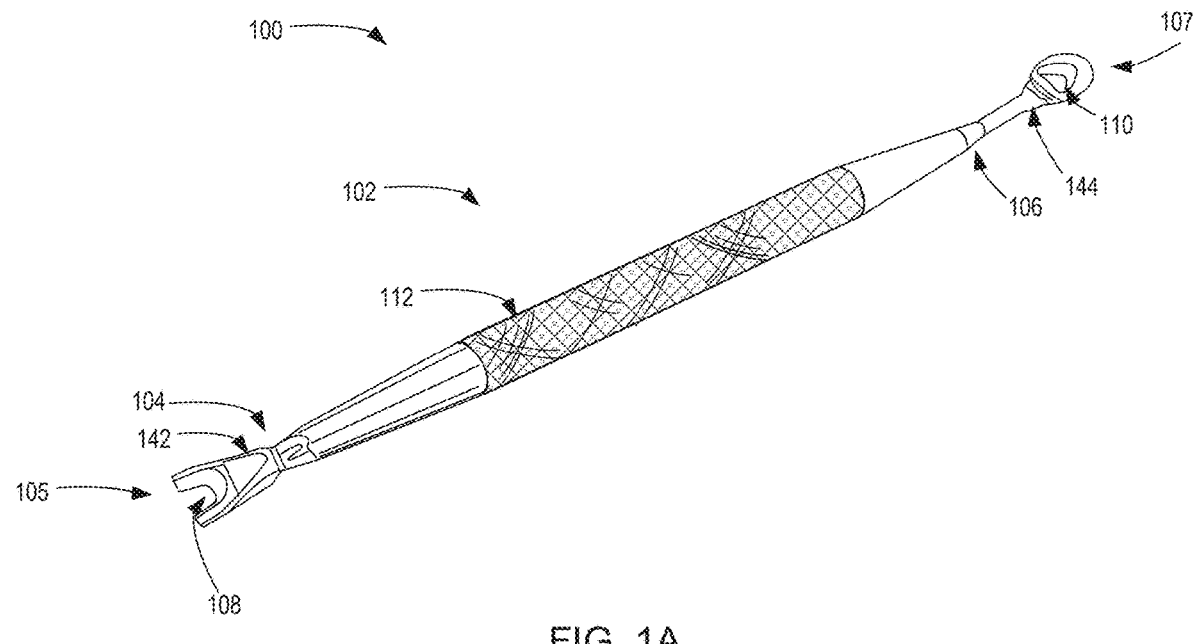
FIGS. 1a and 1b are schematic views of a device for removing molluscum contagiosum according to one aspect or embodiment of the present invention.

The following description is provided to enable those skilled in the art to make and use the described embodiments contemplated for carrying out the invention. Various modifications, equivalents, variations, and alternatives, however, will remain readily apparent to those skilled in the art. Any and all such modifications, variations, equivalents, and alternatives are intended to fall within the spirit and scope of the present invention.

For purposes of the description hereinafter, the terms "upper," "lower," "right," "left," "vertical," "horizontal," "top," "lower," "lateral," "longitudinal," and derivatives thereof shall relate to the invention as it is oriented in the drawing figures. However, it is to be understood that the invention may assume various alternative variations, except where expressly specified to the contrary. It is also to be understood that the specific devices illustrated in the attached drawings, and described in the following specification, are simply exemplary embodiments of the invention. Hence, specific dimensions and other physical characteristics related to the embodiments disclosed herein are not to be considered as limiting.

Also, as used herein, the articles "a" and "an" are intended to include one or more items and may be used interchangeably with "one or more" and "at least one." Where only one item is intended, the term "one" or similar language is used. Also, as used herein, the terms "has," "have," "having," or the like are intended to be open-ended terms.

Figure 1B:
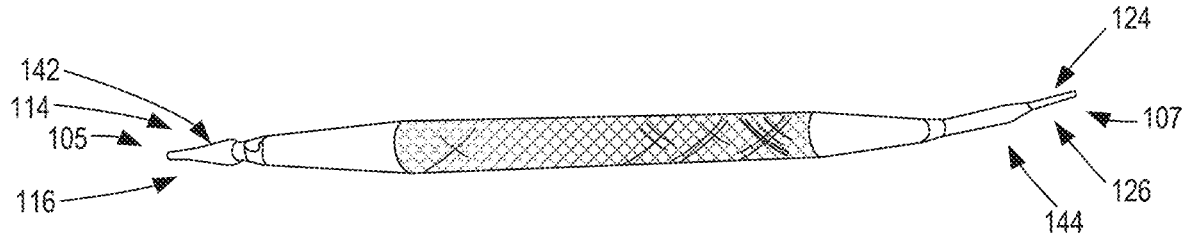

Referring to FIGS. 1a and 1b, a device 100 for removing molluscum contagiosum according to one aspect or embodiment of the present application is shown. The device 100 includes an elongated body 102. The elongated body 102 may include a first end 104, and a second end 106. The elongated body 102 may extend in a first direction and a second direction opposite the first direction, such that the elongated body 102 terminates on the first end 104 and the second end 106. The elongated body 102 may be of any shape, size, or dimension. For example, the elongated body 102 may be in the shape of cylinder, prism, rectangular box, etc., or any combination of various shapes. For example, the elongated body may be of a size that is suitable or easy for a user to grab and hold with one hand. The elongated body 102 may include as grip portion 112. The grip portion 112 may be engraved into the elongated body 102 via a pattern, such as a mesh pattern, so as to increase a user's ability to grip the device 100. The grip portion 112 may prevent the device 100 from slipping out of the hand of a user. The device 100 may be made of any suitable material. The suitable material may be any metal, alloys, plastic material, biodegradable materials or any combinations thereof. For example, metal and alloys may be aluminum, metal alloys, and medical grade stainless steel. Plastic material may be any medical grade plastic, biocompatible plastic, biodegradable plastics, or any combinations of thereof.

With continued reference to FIGS. 1a and 1b, the elongated body 102 may decrease in size or circumference as it extends in the first and second directions toward the first end 104 and/or the second end 106. The device 100 may include a first cutting end 105 and a second cutting end 107. The first cutting end 105 and the second cutting end 107 may extend from the elongated body 102. For example, the first cutting end 105 may extend in the first direction from the first end 104 of the elongated body 102, and the second cutting end 107 may extend in the second direction from the second end 106 of the elongated body. The first cutting end 105 and the second cutting end 107 may extend in the same direction as the extension of the elongated body 102 such that the first cutting end 105, the second cutting end 107, and the elongated body 102 form a substantially straight profile. Alternatively, the first cutting end 105 and/or the second cutting end 107 may extend from the elongated body 102 at an angle. For example, referring to FIG. 1b the second cutting end 107 may extend at an angle from the elongated body 102. In this manner, the first end 105, the second end 106, and the elongated body 102 do not form a substantially straight profile.

With continued reference to FIGS. 1a and 1b, the first cutting end may be removably attached to the elongated body 102 of the device 100. Alternatively, the first cutting end 105 may be permanently fixed to the elongated body 102 of the device 100. The first cutting end 105 may include a first cutting edge 108, an upper surface 114, a lower surface 116, and a contact portion 142. The lower surface 116 may be substantially flat. The second cutting end 107 may be removably attached to the second end 106 of the elongated body 102. Alternatively, the second cutting end 107 may be permanently fixed to the elongated body 102 of the device

4

100. The second cutting end may include a second cutting edge 110, an upper surface 124, a lower surface 126, and a contact portion 144.

Figure 2A:
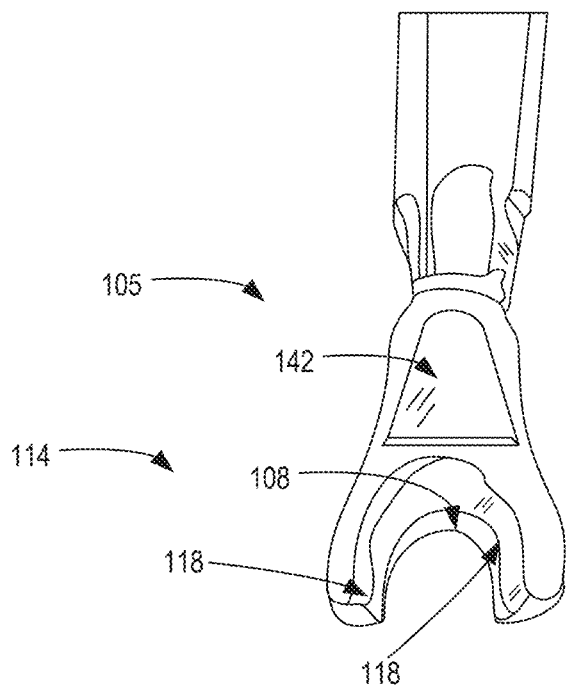
FIGS. 2a and 2b are enlarged perspective view of one end of the device according to FIGS. 1a and 1b.
Figure 2B:
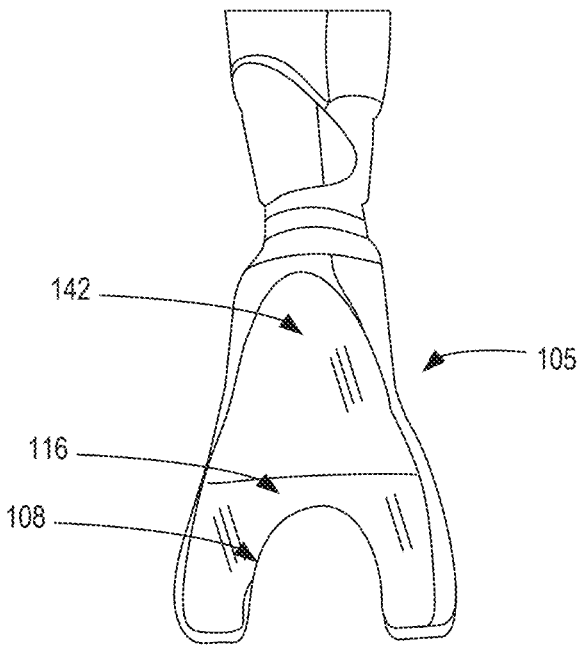

Referring to FIGS. 2a and 2b, the first cutting end 105 according to one aspect or embodiment of the present invention is shown. The first cutting edge 108 of the first cutting end 105 may be configured to cut or remove molluscum contagiosum. The first cutting end 105 may include a slope 118. The slope may extend in the first direction from the upper surface 114 of the first end 105 to the lower surface 116 of the first end 105. In this manner, the slope 118 of the first end 105 is pointing downward as the first cutting end 105 extends in the first direction. The slope 118 may be of any gradient. The gradient may vary as the slope 118 extends in the first direction. For example, the gradient may be steep at the outset and may eventually decrease as the slope 118 extends in the first direction.

With continued reference to FIGS. 2a and 2b, the slope 118 may terminate at the lower surface 116 of the first end 105 to form the first cutting edge 108. The first cutting edge 108 may be of any shape. For example, referring to FIG. 2a, the first cutting edge 108 may resemble a semi-circle, in which a molluscum contagiosum may be placed when in use prior to removing a lesion. The first cutting edge 108 may be of other shapes to conform to the shape of molluscum contagiosum or other lesions to be removed. For example, the first cutting edge 108 may be a straight line, an open square, a curvy line, etc.

With continued reference to FIGS. 2a and 2b, the first cutting end 105 may include a contact portion 142. The contact portion 142 may protrude from the first cutting end 105 and be placed between the first cutting edge 108 and the elongated body 102. The contact portion 142 may protrude from the upper surface 114 and/or the lower surface 116 of the first cutting end 105. The protrusion of the contact portion 142 may be of any shape to allow substantially only the lower surface 116 of the first cutting end 105 that forms the first cutting edge 108 to be in contact with skin of a person when in use when the user lifts the elongated body 102 and presses the first cutting end 105 against the skin.

Figure 3A:
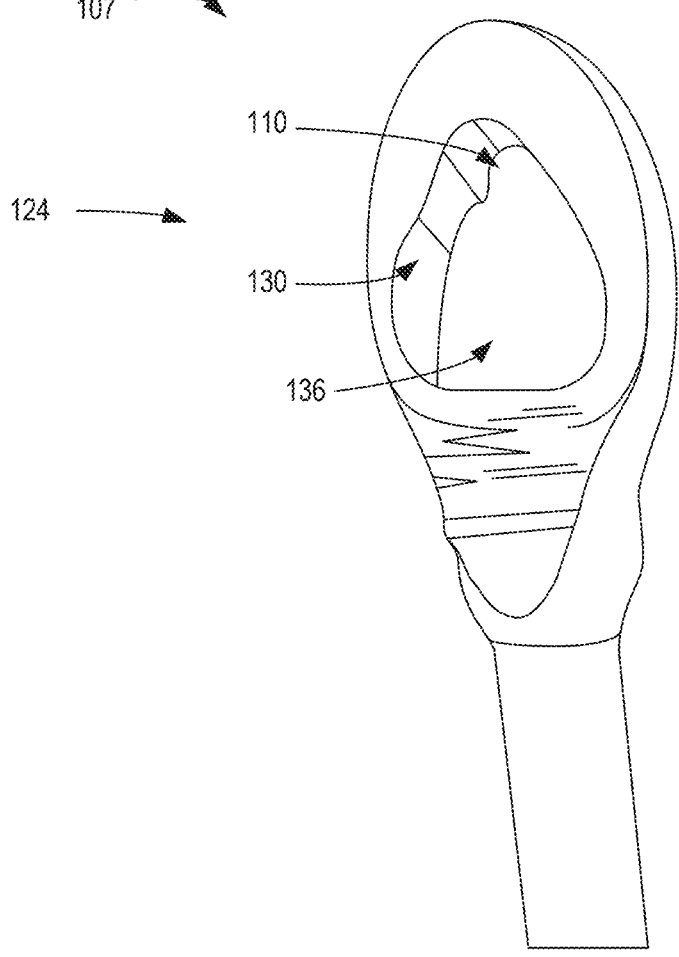
FIGS. 3a and 3b are enlarged perspective view of the other end of the device according to FIGS. 1a and 1b.
Figure 3B:
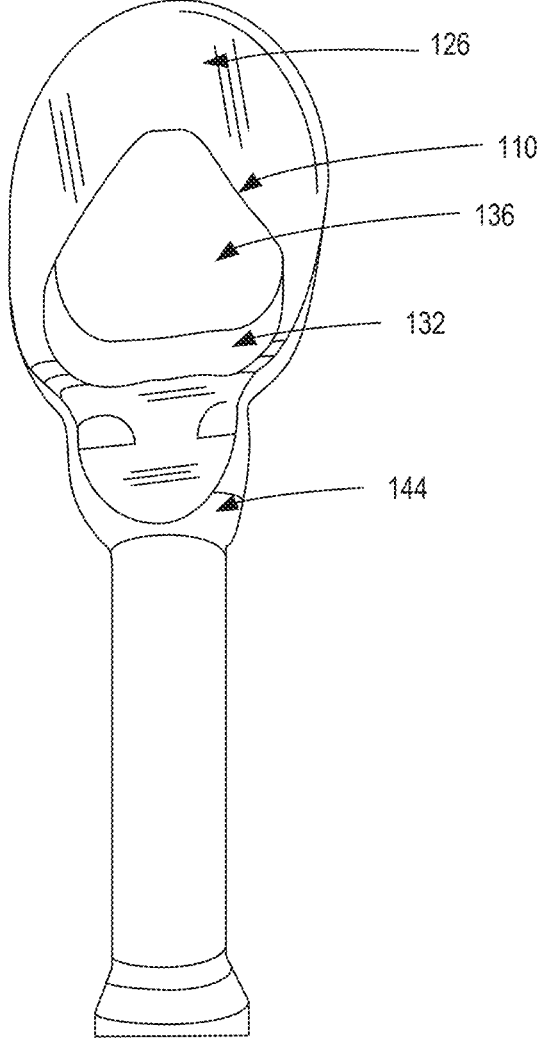

Referring to FIGS. 3a and 3b, the second cutting end 107 according to one aspect or embodiment of the present invention is shown. The second cutting edge 110 of the second cutting end 107 may be configured to cut or remove molluscum contagiosum. The second cutting end 107 may include a first side surface 130 and a second side surface 132. The first and the second side surfaces 130, 132 may extend in the second direction from the lower surface 126 of the second cutting end 106 to the upper surface 124 of the second cutting end 105. The first and second side surfaces 130, 132 may be of any gradient. The gradient may vary as the first and the second side surface 130, 132 extend in the second direction. For example, the gradient of the first and the second side surfaces 130, 132 may be identical, as to form parallel surfaces.

With continued reference to FIGS. 3a and 3b, the first side surface 130 and the second side surface 132 may be form an opening 136 there between. The shape of the opening 136 may be determined by the shapes and the gradient of the first and second side surfaces 130, 132. The opening 136 may receive any molluscum contagiosum or any lesions to be removed. The opening 136 may be any shape. For example, the opening 136 may be a rectangle, a circle, a semi-circle, or any other irregular shape.

With continued reference to FIGS. 3a and 3b, a portion of the first side surface 130 may form the second cutting edge 110. For example, the second cutting edge 110 may be formed at the intersection of the lower surface 126 of the second end 106 and where the first side surface 130 begins to extend in the second direction. The second cutting edge 110 may be of any shape to conform to the shape of the molluscum contagiosum or any lesions. The second cutting edge 138 may be flat, straight, curved, rounded, etc. The second side surface 132 may be of any shape. The second side surface 132 may be a straight line, a curve, rounded, etc.

With continued reference to FIGS. 3a and 3b, the lower surface 126 of the second end 106 may be configured to be in contact with the skin of a person. The lower surface 126 may be a substantially flat surface. The second cutting end 107 may include a contact portion 144. The contact portion 144 may protrude from the upper surface 124 and/or the lower surface 126 of the second cutting end 107. The contact portion 144 may be configured to allow only the second cutting end 107 to be in contact with skin of a person when the user lifts the elongated body 102 and presses the second cutting end 106 against the skin. Alternatively, the second cutting end 107 may extend from the elongated body 102 at an angle such that only the second cutting end is in contact with the skin of a person when in use without having the elongated body 102 lifted.

Figure 4A:
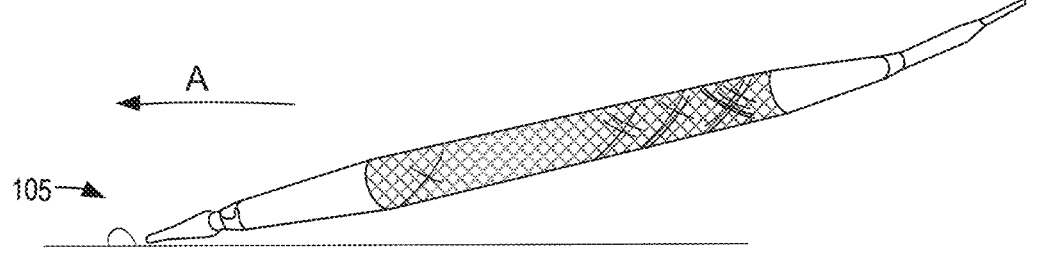
FIGS. 4a and 4b are perspective view of the device for removing molluscum contagiosum according to one aspect or embodiment of the present invention.
Figure 4B:
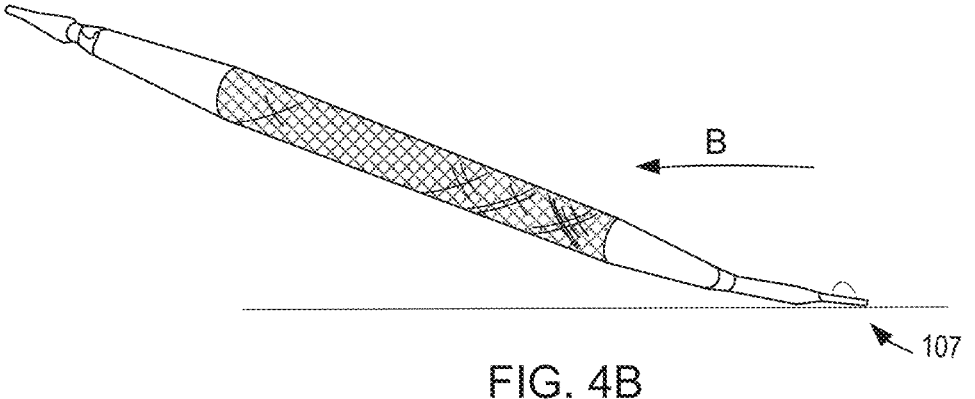

Referring to FIGS. 4a and 4b, in use, according to one aspect or embodiment of the present invention, a molluscum contagiosum may be removed. A user may place the device on a skin of a person such that the first cutting edge 108 is placed in vicinity of the molluscum contagiosum. The elongated body 102 of the device 100 may be lifted such the first end 104 of the device is in contact with the skin of the person. For example, the lower surface 116 and the contact portion 142 may be in contact with the skin of the person. The device 100 may be moved laterally, in the direction of arrow A as shown in FIG. 4a, such that the first cutting edge 108 moves towards the molluscum contagiosum. For example, the user may move the device 100 in the first direction. As the first cutting edge 108 moves towards the molluscum contagiosum, the molluscum contagiosum may be placed slope 118 of the first cutting end 105. As the device 100 continues to move laterally past the molluscum contagiosum, the first cutting edge 108 may cut the molluscum contagiosum from the skin of the person.

With continued reference to FIGS. 4a and 4b, in an alternative embodiment, in use a user may place the device 100 on a skin of a person such that the second cutting edge 110 is placed in vicinity of the molluscum contagiosum. For example, the molluscum contagiosum may be placed inside the opening 136 of the second cutting end 107. The first side surface 130 and the second side surface 132 may aid in helping the molluscum with placing the molluscum contagiosum in the opening 136 by allowing the molluscum contagiosum to slide down the two surfaces. Once the molluscum contagiosum is placed inside the opening 136, the elongated body 102 of the device 100 may be lifted such that the second cutting end 107 of the device 100 is in contact with the skin of the person. For example, the lower surface 126 and the contact portion 144 may be in contact with the skin of the person. Alternatively, the elongated body 102 of the device may not need be lifted if the second cutting end 107 of the device 100 extends from the second end 106 of the elongated body 102 at an angle. The device 100 may be moved laterally, in the direction of arrow B as shown in FIG. 4b, and towards the molluscum contagiosum. For example, the device 100 may be moved in the first direction. As the device moves, such that the second cutting edge 110 moves towards the molluscum contagiosum, the molluscum contagiosum may be placed on the gradient of the first side surface 130. As the device 100 continues to move laterally past the molluscum contagiosum, the second cutting edge 110 may cut the molluscum contagiosum from the skin of the person.

Although the present disclosure has been described in detail for the purpose of illustration based on what is currently considered to be the most practical and preferred embodiments or aspects, it is to be understood that such detail is solely for that purpose and that the present disclosure is not limited to the disclosed embodiments or aspects, but, on the contrary, is intended to cover modifications and equivalent arrangements that are within the spirit and scope of the appended claims. For example, it is to be understood that the present disclosure contemplates that, to the extent possible, one or more features of any embodiment may be combined with one or more features of any other embodiment. For example, the present disclosure describes a device and method of removing molluscum contagiosum; however, it is to be understood that the present disclosure may also describe a device and removing any type of skin abnormalities or lesions, such as acne.

What is claimed is:

1. A device for removing lesions, the device comprising:
an elongated body extending in a first direction and a second direction opposite to the first direction, the elongated body terminating at a first end and a second end;
a first cutting end at the first end of the elongated body, the first cutting end having a first cutting edge, an upper surface, and a substantially flat lower surface; and
a second cutting end at the second end of the elongated body having an upper surface, a lower surface, and a second cutting edge,
wherein the first cutting end comprises a slope, the slope extending in the first direction from the upper surface to the substantially flat lower surface of the first cutting end, the slope terminating at the substantially flat lower surface to form the first cutting edge,
wherein the second cutting end comprises a first side surface and a second side surface extending in the second direction from the lower surface to the upper surface of the second cutting end, the first side surface and the second side surface formed between the lower face and upper surface of the second end,
wherein the first side surface and the second side surface are substantially parallel, and
wherein the first side surface terminates at the lower surface of the second end to form the second cutting edge.

2. The device of claim 1, wherein the first cutting end and the second cutting end are removably attached to the elongated body.

3. The device of claim 1, further comprising:
a grip portion, wherein the elongated body comprises the grip portion, and wherein the thickness of the grip portion of the elongated body is constant.

4. The device of claim 1, wherein the first side surface and the second side surface form an enclosed opening, wherein the enclosed opening is configured to receive a lesion, and wherein the first side surface and the second side surface are interconnected.

5. The device of claim 1, wherein the second end comprises a contact portion, wherein the contact portion is configured to lift the elongated body such that the elongated body does not contact skin of a person when the first cutting end or the second cutting end is on contact with the skin of the person.

6. The device of claim 1, wherein the second end extends in the second direction from the elongated body at an angle.

7. The device of claim 1, wherein the opening of the second cutting end narrows as second end extends in the second direction.

8. A method of removing lesions, the method comprising:

placing the first cutting edge of the device of claim 1 on skin of a person in vicinity of a lesion;

lifting the grip portion of the device such that only the contact portion of the first end and the first end of the device are in contact with the person; and moving the first cutting edge laterally and in parallel with the skin of the person towards the lesion.

9. A method of removing lesions, the method comprising:

placing the second cutting edge of the device of claim 1 on skin of a person in vicinity of a lesion, wherein the lesion is placed inside the opening;

lifting the grip of the device such that only the contact portion of the second end and the second end of the device are in contact with the person; and moving the second cutting edge laterally and in parallel with the skin of the person towards the lesion.

* * * * *